United States Patent [19]

Langbein et al.

[11] 4,145,427

[45] Mar. 20, 1979

[54] N-[1-(3-BENZOYL-PROPYL)-4-PIPERIDYL]-SULFONIC ACID AMIDES AND SALTS THEREOF

[75] Inventors: Adolf Langbein; Karl-Heinz Weber, both of Gau-Algesheim; Karin Böke, Ingelheim am Rhein, all of Fed. Rep. of Germany

[73] Assignee: Boehringer Ingelheim GmbH, Ingelheim am Rhein, Fed. Rep. of Germany

[21] Appl. No.: 896,575

[22] Filed: Apr. 14, 1978

[30] Foreign Application Priority Data

Apr. 26, 1977 [DE] Fed. Rep. of Germany ....... 2718405

[51] Int. Cl.² .................... A61K 31/18; A61K 31/44; C07D 211/96
[52] U.S. Cl. .................................. 424/267; 546/206; 546/194; 546/223; 546/213
[58] Field of Search ........... 260/239.8, 293.73, 293.68, 260/293.69; 424/267

[56] References Cited

U.S. PATENT DOCUMENTS

| 3,209,006 | 9/1965 | Wragg et al. | 260/293.73 |
| 3,932,636 | 1/1976 | Cross et al. | 424/267 X |
| 3,932,647 | 1/1976 | Holland | 424/267 |
| 3,932,649 | 1/1976 | Cross et al. | 424/267 |

*Primary Examiner*—John D. Randolph
*Attorney, Agent, or Firm*—Hammond & Littell

[57] ABSTRACT

Compounds of the formula

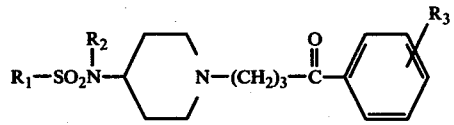

wherein
  $R_1$ is alkyl of 1 to 6 carbon atoms, phenyl, substituted phenyl or heteroaryl;
  $R_2$ is hydrogen or alkyl; and
  $R_3$ is hydrogen, methyl, methoxy or halogen;
and non-toxic, pharmacologically acceptable acid addition salts thereof. The compounds are useful as neuroleptics.

6 Claims, No Drawings

N-[1-(3-BENZOYL-PROPYL)-4-PIPERIDYL]-SULFONIC ACID AMIDES AND SALTS THEREOF

This invention relates to novel N-[1-(3-benzoyl-propyl)-4-piperidyl]-sulfonic acid amides and acid addition salts thereof, as well as to methods of preparing these compounds.

More particularly, the present invention relates to a novel class of compounds represented by the formula

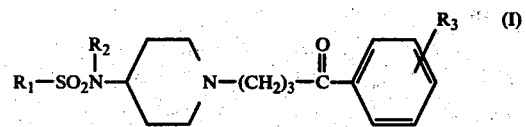

wherein
$R_1$ is alkyl of 1 to 6 carbon atoms, phenyl, substituted phenyl or heteroaryl;
$R_2$ is hydrogen or alkyl; and
$R_3$ is hydrogen, methyl, methoxy or halogen;
and non-toxic, pharmacologically acceptable acid addition salts thereof.

The compounds embraced by formula I may be prepared by the following methods:

Method A

By alkylating an amido-piperidine of the formula

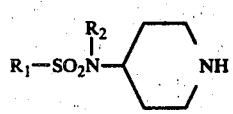

wherein $R_1$ and $R_2$ have the same meanings as in formula I, with a butyrophenone derivative of the formula

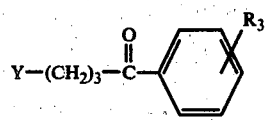

wherein
$R_3$ has the same meanings as in formula I, and
Y is a substituent which can be split off under the reaction conditions, especially the anion of a strong inorganic or organic acid, such as hydrochloric acid, hydrobromic acid, hydroiodic acid, benzoylsulfonic acid, toluene sulfonic acid or an alkylsulfonic acid.

The alkylating agent of the formula III is provided in the stoichiometric amount or in excess thereover, and the reaction is advantageously performed in the presence of an acid-binding agent, such as triethylamine, N,N-dicyclohexylethylamine, sodium carbonate, potassium carbonate, calcium oxide or preferably sodium bicarbonate.

Although the presence of solvent is not essential, it is advantageous to perform the reaction in an inert solvent medium, such as chloroform, toluene, ethanol, nitromethane, tetrahydrofuran or preferably dimethylformamide.

The reaction temperature may be varied within wide limits; however, temperatures between 50° and 150° C. are most advantageous, and 100° C. is preferred. The addition of catalytic to equimolar amounts of potassium iodide or sodium iodide to the reaction mixture is of advantage.

Method B

By acylating a compound of the formula

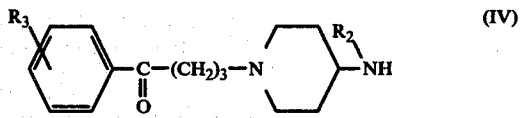

wherein $R_2$ and $R_3$ have the same meanings as in formula I, with a sulfonic acid chloride of the formula

wherein $R_1$ has the same meanings as in formula I.

The reaction is performed in any conventional solvent, such as chloroform, benzene, tetrahydrofuran or the like, and preferably in dimethylformamide. The reaction temperature may be varied within wide limits, and advantageously between 20° and 100° C. The addition of an acid-binding agent, such as triethylamine, N,N-dicyclohexyl-ethylamine, sodium carbonate, potassium carbonate or preferably sodium bicarbonate, is of advantage.

Method C

For the synthesis of a compound of the formula I wherein $R_2$ is alkyl, by alkylating a compound of the formula

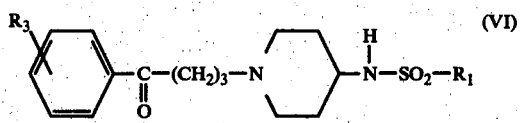

wherein $R_1$ and $R_3$ have the same meanings as in formula I, with an alkylating agent of the formula

wherein
$R_2$ is alkyl, and
X is halogen or the residue of a sulfuric acid semiester.

The reaction is advantageously performed in the presence of a base such as sodium hydroxide.

The end products obtained by methods A to C are isolated from the reaction mixture by conventional laboratory methods. If required, the raw products thus obtained may be purified, for example by column-chromatography, before crystallizing them in the free base form or as acid addition salts.

The compounds embraced by formula I are organic bases and therefore form acid addition salts with inorganic or organic acids. Examples of non-toxic, pharmacologically acceptable acid addition salts are those formed with a hydrohalic acid, nitric acid, sulfuric acid, orthophosphoric acid, oxalic acid, citric acid, tartaric acid, fumaric acid, maleic acid, propionic acid, butyric acid, acetic acid, methanesulfonic acid, toluenesulfonic acid, sulfanilic acid, succinic acid, 8-chlorotheophlline or the like.

The starting compounds of the formula II for method A are new. They may be prepared by reacting 4-amino-1-benzyl-piperidine of the formula

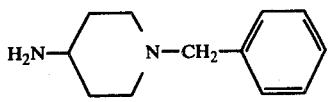

with a sulfonic acid chloride of the formula $$R_1\text{—}SO_2\text{—}Cl \tag{IX}$$

wherein $R_1$ has the same meanings as in formula I, to form a sulfonamide of the formula

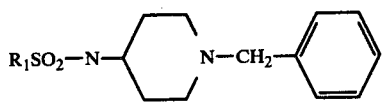

wherein $R_1$ has the meanings defined above, and hydrogenating the sulfonamide intermediate as illustrated in Example A below.

The starting compounds of the formula IV can be prepared by the process described in British Pat. No. 1,345,872.

The other starting compounds are all disclosed in the prior art.

The following examples illustrate the present invention and will enable others skilled in the art to understand it more completely. It should be understood, however, that the invention is not limited solely to the particular examples given below.

EXAMPLE A

N-Piperidyl-methanesulfonamide hydrochloride (a) 190.3 gm (1 mol) of 1-benzyl-4-amino-piperdine were dissolved in 2 liters of methylene chloride, and the solution was slowly admixed over a period of 30 minutes with 126 gm (1 mol) of methanesulfonic acid chloride. The resulting mixture was allowed to react for one hour, and after cooling it the precipitated substance was collected by suction filtration. The filter cake was washed twice with 500 ml of methylene chloride each, then thoroughly suction-dried, and crystallized from methanol, yielding 243 gm (about 80% of theory) of (1-benzyl-4-piperdyl)-methanesulfonamide hydrochloride, m.p. 246°–247° C.

(b) 304.8 gm (1 mol) of (1-benzyl-4-piperidyl)-methanesulfonamide hydrochloride were dissolved in a mixture of 2500 ml methanol and 600 ml water, and the solution was hydrogenated at 5 atmospheres gauge and 50° C. in the presence of palladium-on-charcoal until the absorption of hydrogen ceased. Thereafter, the catalyst was separated by suction filtration, the filtrate was evaporated, the residue was admixed with 200 ml of ethanol/benzene (1:1), and the mixture was evaporated in a slight vacuum. The latter dissolution and evaporation procedure was repeated once, and the dry residue was boiled briefly with 850 ml of ethanol. After cooling, the residual crystalline substance was collected by suction filtration, yielding 209 gm (97.6% of theory) of N-piperdyl-methanesulfonamide hydrochloride, m.p. 279°–281° C.

The following compounds of the formula II were obtained in analogous manner:

N-piperidyl-toluenesulfonamide hydrochloride, m.p. 271°–273° C.

N-piperidyl-ethanesulfonamide hydrochloride, m.p. 236°–237° C.

N-piperidyl-benzenesulfonamide hydrochloride, m.p. 250°–251° C.

N-piperidyl-thiophenesulfonamide hydrochloride, m.p. 275°–280° C.

EXAMPLE 1

N-[1-(3-p-Fluorobenzoyl-propyl)-4-piperidyl]-methanesulfonamide hydrochloride by method A A mixture consisting of 21.5 gm (0.1 mol) of N-piperidyl-methanesulfonamide hydrochloride, 26.9 gm (0.1 mol) of the ethylene ketal of 4-chloro-4'-fluorophenyl-butyrophenone, 25.4 gm (0.3 mol) of sodium bicarbonate, 5 gm of potassium iodide and 250 ml of dimethylformamide was heated at 100° C. for 2 hours, while stirring. Thereafter, the solvent was removed at 70° C. in a rotary evaporator, the residue was taken up in 200 ml of ethyl acetate/ether (1:1), and the mixture was washed twice with 100 ml of water each. The organic phase was extracted three times with 150 ml of 1 N hydrochloric acid each, and the combined hydrochloric acid extracts were heated at 50° C. for 30 minutes. After cooling, the solution was washed twice with 500 ml of ether each, made alkaline with 50 ml of concentrated ammonia while cooling on ice, and extracted three times with 100 ml of methylene chloride each. The organic phase was dried over sodium sulfate and then filtered through 10 gm of silica gel. The filtrate was evaporated in a rotary evaporator, the residue was dissolved in methanol, the solution was admixed with a slight excess of methanolic hydrochloric acid and then with ether, so that the turbidity just disappeared again. 26.5 gm (59% of theory) of the compound of the formula

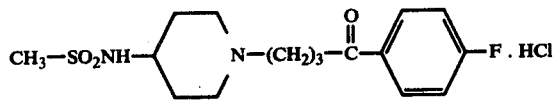

with a melting point of 197°–199° C. were obtained.

The hydrochlorides of the compounds of the formula I listed in the following table were prepared in analogous manner:

| $R_1$ | $R_2$ | $R_3$ | Yield % | M.p. ° C |
|---|---|---|---|---|
|  | H | 4-F | 13 | 192–194 |
| CH₃—⟨phenyl⟩— |  |  |  |  |
|  | H | 4-F | 82 | 173–175 |
| ⟨phenyl⟩— |  |  |  |  |
|  | H | 4-F | 89 | 224–227 |
| 2,4-dimethylphenyl |  |  |  |  |

-continued

| $R_1$ | $R_2$ | $R_3$ | Yield % | M.p. °C |
|---|---|---|---|---|
| 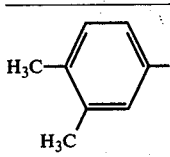 | H | 4-F | 81 | 185–187 |
| 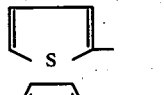 | H | 4-F | 40 | 185–186 |
| 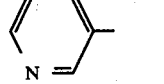 | H | 4-F | 30 | 197–200 |
| 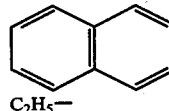 | H | 4-F | 73 | 177–181 |
| $C_2H_5-$ | H | 4-F | 41 | 191–192 |
| $n\text{-}C_4H_9-$ | H | 4-F | 43 | 175–176 |
| $CH_3-$ | $CH_3$ | 4-F | 31 | 225–228 |

The compounds of the present invention, that is, those embraced by formula I above and their non-toxic, pharmacologically acceptable acid addition salts, have useful pharmacodynamic properties. More particularly, they exhibit neuroleptic activity in warm-blooded animals, such as mice and rats.

In the animal test, known neuroleptics are characterized, inter alia, by antagonistic activities against amphetamine, apomorphine and adrenaline. Besides, they show in the animal test pronounced cataleptic properties. In man they produce, beside their antipsychotic activity, disturbances of an extrapyramidal-motoric nature in a more or less pronounced manner, especially in cases of long-term administration, and at higher doses disturbances resembling the picture of Parkinson's disease. In constrast thereto, the compounds according to this invention shown in the mouse and the rat a strong adrenalin-antagonism, but amphetamine- and apomorphine-antagonistic activities are absent. Besides a strong attenuating activity in behavioral tests, such as the perforated plywood test, the novel compounds — contrary to the above cited preparations known from the literature — exhibit no or only extremely weak cataleptic properties. In accordance with prevailing teachings, it is to be expected with such an activity spectrum, that the compounds according to the invention exert only slight side-effects upon the extrapyramidal-motoric system, which is of great advantage over the preparations of the butyrophenone group on the market.

For pharmaceutical purposes the compounds of the present invention are administered to warm-blooded animals peorally, parenterally or rectally as active ingredients in customary dosage unit compositions, that is, compositions in dosage unit form consisting essentially of an inert pharmaceutical carrier and one effect dosage unit of the active ingredient, such as tablets, coated pills, capsules, wafers, powers, solutions, suspensions, emulsions, syrups, suppositories and the like. One effective dosage unit of the compounds according to the present invention is from 0.0083 to 0.17 mgm/kg body weight, preferably 0.016 to 0.083 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 2

Tablets

The tablet composition is compounded from the following ingredients:

| | |
|---|---|
| N-[1-(3-p-Fluorobenzoyl-propyl)-4-piperidyl]-methanesulfonamide hydrochloride | 2.0 parts |
| Lactose | 55.0 parts |
| Corn starch | 38.0 parts |
| Soluble starch | 4.0 parts |
| Magnesium stearate | 1.0 parts |
| Total | 100.0 parts |

Preparation

The active ingredient and the magnesium stearate are intimately admixed, the mixture is granulated with an aqueous solution of the soluble starch, and the granulate is dried and intimately admixed with the lactose and the corn starch. The resulting composition is compressed into 100 mgm-tablets in a conventional tablet making machine. Each tablet is an oral dosage unit composition containing 2 mgm of the active ingredient.

EXAMPLE 3

Coated Pills

The pill core composition is compounded from the following ingredients:

| | |
|---|---|
| N-[1-(3-p-Fluorobenzoyl-propyl)-4-piperidyl]-thiophenesulfonamide hydrochloride | 2.0 parts |
| Lactose | 28.5 parts |
| Corn starch | 17.0 parts |
| Gelatin | 2.0 parts |
| Magnesium stearate | 0.5 parts |
| Total | 50.0 parts |

Preparation

The active ingredient is intimately admixed with the corn starch, the mixture is moistened with an aqueous 10% solution of the gelatin, the moist mass is granulated through a 1 mm-mesh screen, and the granulate is dried at 40° C. and again passed through the screen. The dry granulate is admixed with magnesium stearate, and the composition is compressed into 50 mgm-pill cores which are then coated in conventional manner with a thin shell consisting essentially of a mixture of sugar, titanium dioxide, talcum and gum arabic. The coated pills are finally polished with beeswax. Each coated pill is an oral dosage unit composition containing 2 mgm of the active ingredient.

EXAMPLE 4

Hypodermic Solution

The solution is compounded from the following ingredients:

| | |
|---|---|
| N-[1-(3-p-Fluorobenzoyl-propyl)-4-piperidyl]-N-methyl-methanesulfonamide hydrochloride | 2.0 parts |
| Sodium chloride | 18.0 parts |
| Distilled water    q.s.ad | 2000.0 parts |

| -continued | |
|---|---|
| | by vol. |

Preparation

The active ingredient and the sodium chloride are dissolved in the distilled water, the solution is filtered until free from suspended particles, and the filtrate is filled into 2 cc-ampules under aseptic conditions. The filled ampules are then sterilized and sealed. Each ampule contains 2 mgm of the active ingredient, and the contents thereof are an injectable dosage unit composition.

Any one of the other compounds embraced by formula I or a non-toxic, pharmacologically acceptable acid addition salt thereof may be substituted for the particular piperidine compound in Examples 2 through 4. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily appraent to others skilled in the art that the invention is not limited to these particular embodiments, and that various changes and modifications may be made without departing from the spirit of the invention or the scope of the appended claims.

We claim:

1. A compound of the formula

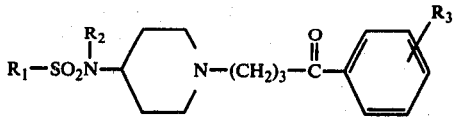

wherein
$R_1$ is alkyl of 1 to 6 carbon atoms, phenyl, substituted phenyl, naphthyl or heteroaryl;
$R_2$ is hydrogen or lower alkyl; and
$R_3$ is hydrogen, methyl, methoxy or halogen;
or a non-toxic, pharmacologically acceptable acid addition salt thereof.

2. A compound of claim 1, where
$R_1$ is alkyl of 1 to 4 carbon atoms, phenyl, tolyl, xylyl, naphthyl, thienyl or pyridyl;
$R_2$ is hydrogen or methyl; and
$R_3$ is fluorine;
or a non-toxic, pharmacologically acceptable acid addition salt thereof.

3. A compound of claim 1, which is N-[1-(3-p-fluorobenzoyl-propyl)-4-piperidyl]-methanesulfonamide or a non-toxic, pharmacologically acceptable acid addition salt thereof.

4. A compound of claim 1, which is N-[1-(3-p-fluorobenzoyl-propyl)-4-piperidyl]-N-methyl-methanesulfonamide or a non-toxic, pharmacologically acceptable acid addition salt thereof.

5. A neuroleptic pharmaceutical dosage unit composition consisting essentially of an inert pharmaceutical carrier and an effective neuroleptic amount of a compound of claim 1.

6. The method of depressing the central nervous system of a warm-blooded animal in need thereof, which comprises perorally, parenterally or rectally administering to said animal an effective neuroleptic amount of a compound of claim 1.

* * * * *